United States Patent
Feng et al.

(10) Patent No.: US 9,309,229 B2
(45) Date of Patent: Apr. 12, 2016

(54) CRYSTALLINE FORMS OF 5-CHLORO-N2-(2-ISOPROPOXY-5-METHYL-4-PIPERIDIN-4-YL-PHENYL)-N4-[2-(PROPANE-2-SULFONYL)-PHENYL]-PYRIMIDINE-2,4-DIAMINE

(75) Inventors: Lili Feng, Pine Brook, NJ (US); Baoqing Gong, Morris Plains, NJ (US); Piotr H. Karpinski, Lincoln Park, NJ (US); Liladhar Murlidhar Waykole, Succasunna, NJ (US)

(73) Assignee: Novartis AG, Basel (CH)

( * ) Notice: Subject to any disclaimer, the term of this patent is extended or adjusted under 35 U.S.C. 154(b) by 34 days.

(21) Appl. No.: 13/993,217

(22) PCT Filed: Dec. 15, 2011

(86) PCT No.: PCT/US2011/065030
§ 371 (c)(1),
(2), (4) Date: Jun. 11, 2013

(87) PCT Pub. No.: WO2012/082972
PCT Pub. Date: Jun. 21, 2012

(65) Prior Publication Data
US 2013/0274279 A1    Oct. 17, 2013

Related U.S. Application Data (60) Provisional application No. 61/424,194, filed on Dec. 17, 2010.

(51) Int. Cl.
*C07D 239/02* (2006.01)
*C07D 403/12* (2006.01)
*A61K 31/505* (2006.01)
*C07D 401/12* (2006.01)

(52) U.S. Cl.
CPC ............ *C07D 403/12* (2013.01); *C07D 401/12* (2013.01)

(58) Field of Classification Search
CPC ... A61K 31/505; C07D 239/02; C07D 403/12
USPC ......................................... 514/275; 544/323
See application file for complete search history.

(56) References Cited

U.S. PATENT DOCUMENTS

2008/0176881 A1    7/2008    Michellys

FOREIGN PATENT DOCUMENTS

| EP | 2311807 A1 | 4/2011 |
| WO | WO03078404 A1 | 9/2003 |
| WO | 2008/073687 | * 6/2008 |
| WO | 2008/073687 A2 | 6/2008 |
| WO | 2008073687 A2 | 6/2008 |
| WO | 2009126515 A1 | 10/2009 |
| WO | 2011072696 A1 | 6/2011 |
| WO | 2012082580 A2 | 6/2012 |
| WO | 2012083306 A2 | 6/2012 |
| WO | WO2012/082972 | 6/2012 |

OTHER PUBLICATIONS

Remington Pharmacy, Chapter 38—Preformulation, 20th edition, Lippincott, Williams & Wilkins, pp. 705-714, (2000).
Cains Peter W., "Classical Methods of Preparation of Polymorphs and Alternative Solid Forms", Polymorphism in pharmaceutical solids by Harry Brittain, Informa Healthcare USA, Inc.; New York; 2009, pp. 106-107 and pp. 116-117, (2009).

* cited by examiner

*Primary Examiner* — James O Wilson
*Assistant Examiner* — Ebenezer O Sackey
(74) *Attorney, Agent, or Firm* — Gregory Houghton (57) ABSTRACT

The present invention describes specific crystalline forms of 5-chloro-N-(2-isopropoxy-5-methyl-4-(piperidin-4-ylphenyl)-N-2-(isopropylsulfonyl)phenyl)-2,4-diamine. The present invention further relates to methods for preparing said crystalline forms, pharmaceutical compositions comprising said crystalline forms, and methods of using said crystalline forms and pharmaceutical compositions to treat disease.

26 Claims, 6 Drawing Sheets

CRYSTALLINE FORMS OF 5-CHLORO-N2-(2-ISOPROPOXY-5-METHYL-4-PIPERIDIN-4-YL-PHENYL)-N4-[2-(PROPANE-2-SULFONYL)-PHENYL]-PYRIMIDINE-2,4-DIAMINE

FIELD OF THE INVENTION

The present invention is directed to crystalline forms of 5-Chloro-N2-(2-isopropoxy-5-methyl-4-piperidin-4-yl-phenyl)-N4-[2-(propane-2-sulfonyl)-phenyl]-pyrimidine-2,4-diamine, methods of making the same, pharmaceutical compositions comprising the same and methods of treatment using the same.

BACKGROUND

Polymorphism denotes the existence of more than one crystalline form of a substance. This ability of a chemical substance to crystallize in more than one crystalline form can have a profound effect on the shelf life, solubility, formulation properties, and processing properties of a drug. In addition, the action of a drug can be affected by the polymorphism of the drug molecule. Different polymorphs can have different rates of uptake in the body, leading to lower or higher biological activity than desired. In extreme cases, an undesired polymorph can even show toxicity. The occurrence of an unknown crystalline form during manufacture can have a significant impact.

Understanding and controlling polymorphism, then, gives a decided advantage in bringing new drugs to the marketplace. First and foremost, predicting any possible polymorphs for a drug product can be used to diminish the possibility of contamination during a drug's manufacture or storage by other polymorphic forms. Failure to catch contamination can have life-threatening consequences in some cases. Crystallizing an unintended polymorph during manufacture can mean weeks or even months of production downtime while scientists find and correct the cause of the new crystalline form or go through another round of testing to obtain approval for the new crystalline form.

Second, understanding which crystalline forms of a drug are possible in certain cases allows researchers to maximize the desired properties of a compound, such as solubility, formulation properties, processing properties, and shelf life. Understanding these factors early in the development of a new drug may mean a more active, more stable, or more cheaply manufactured drug.

The compound 5-Chloro-N2-(2-isopropoxy-5-methyl-4-piperidin-4-yl-phenyl)-N4-[2-(propane-2-sulfonyl)-phenyl]-pyrimidine-2,4-diamine, in the form of a free base, of formula (I)

is an anaplastic lymphoma kinase (ALK) inhibitor, a member of the insulin receptor super family of receptor tyrosine kinases. Compound I was originally described in WO 2008/073687 A1 as Example 7, compound 66.

WO 2008/073687 A1, however, provides no information about crystalline forms of 5-Chloro-N2-(2-isopropoxy-5-methyl-4-piperidin-4-yl-phenyl)-N4-[2-(propane-2-sulfonyl) -phenyl]-pyrimidine-2,4-diamine or its corresponding salts. Crystalline forms of 5-Chloro-N2-(2-isopropoxy-5-methyl-4-piperidin-4-yl-phenyl)-N4-[2-(propane-2-sulfonyl)-phenyl]-pyrimidine-2,4-diamine have been discovered, which are useful in treating diseases which respond to inhibition of anaplastic lymphoma kinase activity, focal adhesion kinase (FAK), zeta-chain-associated protein kinase 70 (ZAP-70) insulin-like growth factor (IGF-1R or a combination thereof. The crystalline forms exhibit new physical properties that may be exploited in order to obtain new pharmacological properties, and that may be utilized in the drug product development of 5-Chloro-N2-(2-isopropoxy-5-methyl-4-piperidin-4-yl-phenyl)-N4-[2-(propane-2-sulfonyl)-phenyl]-pyrimidine-2, 4-diamine.

SUMMARY OF THE INVENTION

The present invention provides substantially pure crystalline forms of 5-Chloro-N2-(2-isopropoxy-5-methyl-4-piperidin-4-yl-phenyl)-N4-[2-(propane-2-sulfonyl)-phenyl]-pyrimidine -2,4-diamine.

The present invention also provides a pharmaceutical composition comprising: (a) a therapeutically effective amount of a substantially pure crystalline form of 5-Chloro-N2-(2-isopropoxy-5-methyl-4-piperidin-4-yl-phenyl)-N4-[2-(propane-2-sulfonyl)-phenyl]-pyrimidine -2,4-diamine; and (b) at least one pharmaceutically acceptable carrier.

The present invention also provides a method for the preparation of a substantially pure crystalline form of 5-Chloro-N2-(2-isopropoxy-5-methyl-4-piperidin-4-yl-phenyl)-N4-[2-(propane-2-sulfonyl)-phenyl]-pyrimidine-2,4-diamine which comprises the step of: reacting 5-Chloro-N2-(2-isopropoxy-5-methyl-4-piperidin-4-yl-phenyl)-N4-[2-(propane-2-sulfonyl) -phenyl]-pyrimidine-2,4-diamine dihydrochloride in a solvent with at least two equivalents of aqueous sodium hydroxide.

The present invention also provides a method for the preparation of a substantially pure crystalline form of 5-Chloro-N2-(2-isopropoxy-5-methyl-4-piperidin-4-yl-phenyl)-N4[2-(propane-2-sulfonyl)-phenyl]-pyrimidine-2,4-diamine which comprises the step of: heating a mixture of two crystalline forms of 5-Chloro-N2-(2-isopropoxy-5-methyl-4-piperidin-4-yl-phenyl)-N4-[2-(propane-2-sulfonyl)-phenyl]-pyrimidine-2,4-diamine in a solvent.

The present invention also provides a method for the treatment of disorders mediated by anaplastic lymphoma kinase, comprising administering to a patient in need of such treatment an effective amount of a substantially pure crystalline form of 5-Chloro-N2-(2-isopropoxy-5-methyl-4-piperidin-4-yl-phenyl)-N4-[2-(propane-2-sulfonyl)-phenyl]-pyrimidine-2,4-diamine.

The present invention also provides the use of a substantially pure crystalline form of 5-Chloro-N2-(2-isopropoxy-5-methyl-4-piperidin-4-yl-phenyl)-N4-[2-(propane-2-sulfonyl)-phenyl]-pyrimidine-2,4-diamine for the preparation of a medicament for the treatment of disorders mediated by anaplastic lymphoma kinase.

The present invention also provides a method for the treatment of disorders selected from benign or malignant tumor; a cancer selected from anaplastic large cell lymphoma; non-Hodgkin's lymphoma; an inflammatory myofibrolastic tumor; a neuroblastoma; sarcoma; lung, non-small cell lung cancer; bronchus; prostate; breast (including sporadic breast cancers and sufferers of Cowden disease); pancreas; gastrointestinal cancer; colon; rectum; colon carcinoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary; multiple myeloma; esophagus; a leukaemia; acute myelogenous leukemia; chronic myelogenous leukemia; lymphocytic leukemia; myeloid leukemia; brain; a carcinoma of the brain; oral cavity and pharynx; larynx; small intestine; and melanoma, comprising administering to a patient in need of such treatment an effective amount of a crystalline form of 5-Chloro-N2-(2-isopropoxy-5-methyl-4-piperidin-4-yl-phenyl)-N4-[2-(propane-2-sulfonyl)-phenyl]-pyrimidine-2,4-diamine.

DETAILED DESCRIPTION OF THE INVENTION

The compound 5-Chloro-N2-(2-isopropoxy-5-methyl-4-piperidin-4-yl-phenyl)-N4-[2-(propane-2-sulfonyl)-phenyl]-pyrimidine-2,4-diamine is obtained in distinct crystalline forms. These "crystalline form(s)" (or "crystalline modification(s)" or "polymorphic form(s)" or "polymorph(s)", as the terms will be used interchangeably herein) differ with respect to thermodynamic stability, physical parameters, x-ray structure and methods of preparation. In addition, "amorphous" refers to a disordered solid state. It should be noted that different samples of a particular crystalline form will share the same major X-ray powder diffraction (XRPD) peaks, but that there can be variation in powder patterns with regard to minor peaks. In addition, the term "about" with regard to XRPD maxima values (in degrees) generally means within 0.3°, more preferably within 0.2°, and most preferably within 0.1° of the given value. Alternatively, the term "about" means (in this and all contexts) within an accepted standard of error of the mean, when considered by one of ordinary skill in the art. As used herein, the term "substantially pure" means that more than 80% of one crystalline form of 5-Chloro-N2-(2-isopropoxy-5-methyl-4-piperidin-4-yl-phenyl)-N4-[2-(propane-2-sulfonyl)-phenyl]-pyrimidine-2,4-diamine or salt thereof is present or isolated, preferably at least 85%, more preferably at least 90%, and most preferably at least 95% of one of the crystalline forms described herein is present.

In one embodiment, a substantially pure crystalline form of 5-Chloro-N2-(2-isopropoxy-5-methyl-4-piperidin-4-yl-phenyl)-N4-[2-(propane-2-sulfonyl)-phenyl]-pyrimidine-2,4-diamine is isolated, referred to as crystalline form A. Form A of the free base is relatively non-hygroscopic at 84% relative humidity (RH) and exhibits minor increase in moisture uptake at 93% RH. It has good solubility at pH 1, fair solubility in water and good solubility in organic solvents (11 mg/mL in pH 1, 0.21 mg/mL in water and 40 mg/mL in methanol, respectively). It is converted to a hydrochloride salt (non-stoichiometric) in pH 1 (0.1N HCl) solution over 72 hour. The pH of 1% suspension in water is 6.86.

Figure 1:
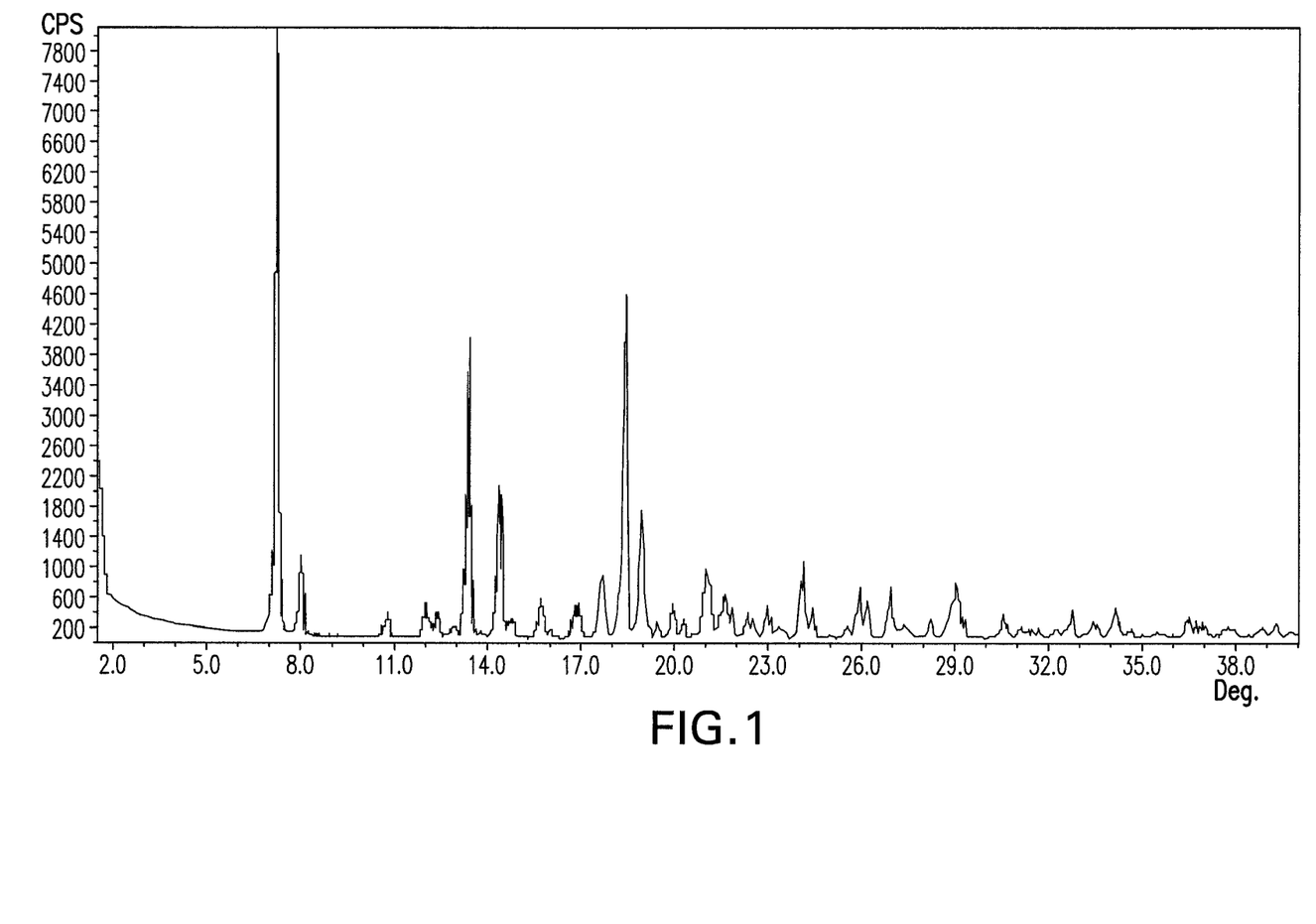
FIG. 1 depicts X-ray powder diffraction pattern for crystalline form A of 5-Chloro-N2-(2-isopropoxy-5-methyl-4-piperidin-4-yl-phenyl)-N4-[2-(propane-2-sulfonyl)-phenyl]-pyrimidine-2,4-diamine. Measurement parameters: Step: 0.020°; Cnt Time: 2.400 Sec.; Range: 1.50-40.40 (Deg); Cont. Scan Rate; 0.50 Deg/min.

The XRPD of crystalline form A of 5-Chloro-N2-(2-isopropoxy-5-methyl-4-piperidin-4-yl-phenyl)-N4-[2-(propane-2-sulfonyl)-phenyl]-pyrimidine-2, 4-diamine exhibits diffraction peaks having maxima at diffraction angles 7.2°, 8.1°, 10.8°, 12.0°, 12.4°, 13.4°, 14.4°, 14.8°, 15.7°, 16.9°, 17.7°, 18.5°, 19.0°, 19.5°, 20.0°, 20.3°, 21.1°, 21.6°, 22.4°, 22.6°, 23.0°, 24.1°, 24.5°, 25.5°, 26.0°, 26.2°, 27.0°, 27.3°, 28.3°, 29.0°, 29.1°, 30.6°, 31.3°, 32.8°, 33.5°, 34.2° and 36.4° (2θ degrees), as summarized by the XRPD pattern in FIG. 1.

Figure 2:
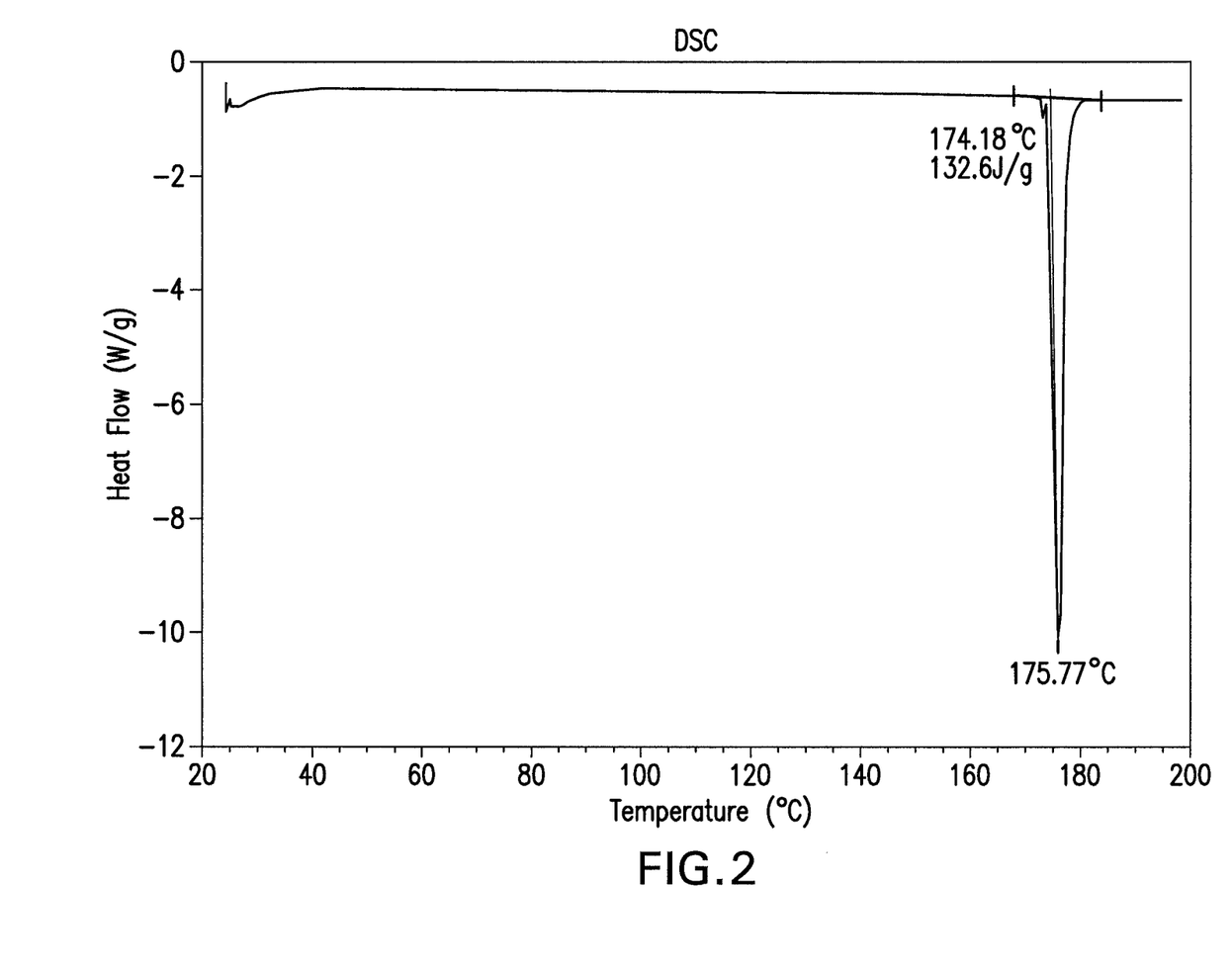
FIG. 2 depicts the differential scanning calorimetry curve for crystalline form A of 5-Chloro -N2-(2-isopropoxy-5-methyl-4-piperidin-4-yl-phenyl)-N4-[2-(propane-2-sulfonyl)-phenyl]-pyrimidine-2,4-diamine.
Figure 3:
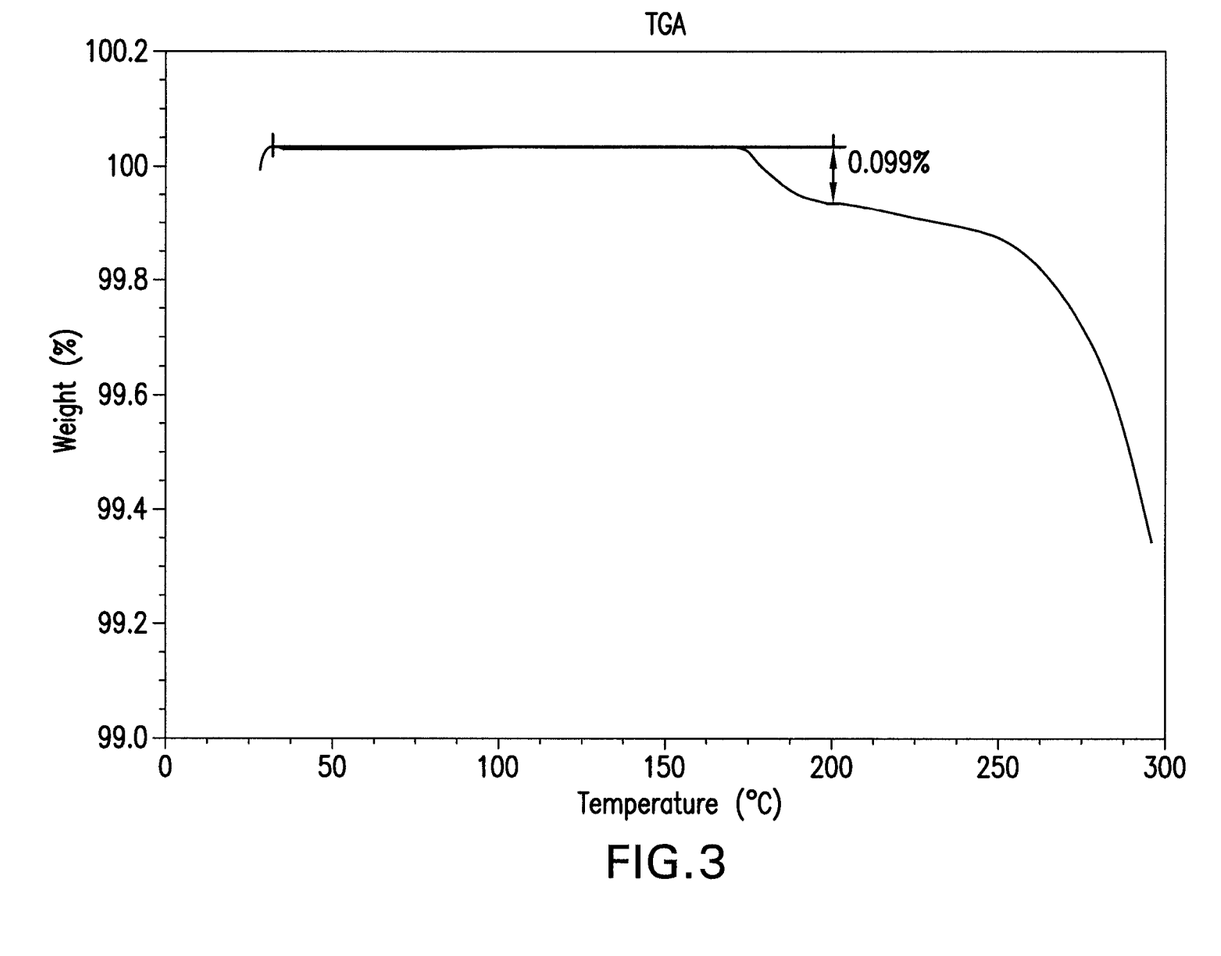
FIG. 3 depicts the thermogravimmetric plot for crystalline form A of 5-Chloro-N2-(2-isopropoxy-5-methyl-4-piperidin-4-yl-phenyl)-N4-[2-(propane-2-sulfonyl)-phenyl]-pyrimidine-2,4-diamine.

Crystalline form A of 5-Chloro-N2-(2-isopropoxy-5-methyl-4-piperidin-4-yl-phenyl)-N4-[2-(propane-2-sulfonyl)-phenyl]-pyrimidine-2, 4-diamine exhibits the following thermal parameters: melting point, Tm (onset) 174° C. as determined by differential scanning calorimetry at a scanning rate of 10° C./min. (FIG. 2), decomposition point, T>250° C., and a weight loss on drying of 0.1% at 200° C., as determined by thermogravimmetric analysis and summarized in FIG. 3.

The Fourier Transform Infrared (FT-IR) spectrum of crystalline form A of 5-Chloro-N2-(2-isopropoxy-5-methyl-4-piperidin-4-yl-phenyl)-N4-[2-(propane-2-sulfonyl)-phenyl]-pyrimidine-2,4-diamine exhibits main bands (in units of wavenumbers, $cm^{-1}$) at 3440.4, 3318.9, 2973.7, 2931.3, 2921.7, 1596.8, 1562.1, 1498.4, 1442.5, 1409.7, 1382.7, 1311.4, 1284.4, 1270.9, 1251.6, 1224.6, 1139.7, 1126.2, 1139.7, 1126.2, 1105.0, 1081.9, 1049.1, 1020.2, 1012.5, 952.7, 937.3, 894.8, 877.5, 860.1, 848.5, 817.7, 798.4, 781.0, 763.7, 756.0, 732.8, 686.6, 665.3, 644.1, 586.3 and 543.8.

In another embodiment, a substantially pure crystalline form of 5-Chloro-N2-(2-isopropoxy-5-methyl-4-piperidin-4-yl-phenyl)-N4-[2-(propane-2-sulfonyl)-phenyl]-pyrimidine-2,4-diamine is isolated, referred to as crystalline form B.

Figure 4:
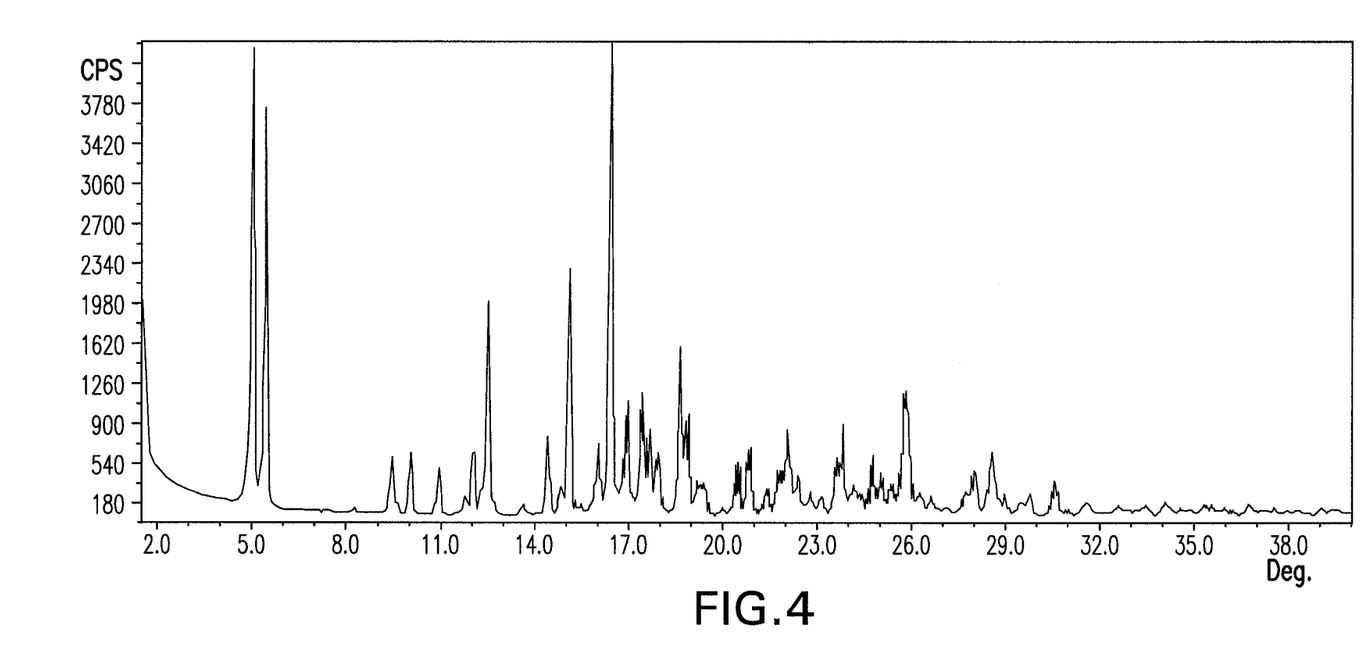
FIG. 4 depicts X-ray powder diffraction pattern for crystalline form B of 5-Chloro-N2-(2-isopropoxy-5-methyl-4-piperidin-4-yl-phenyl)-N4-[2-(propane-2-sulfonyl)-phenyl]-pyrimidine-2,4-diamine. Measurement parameters: Step: 0.020°; Cnt Time: 2.400 Sec.; Range: 1.50-40.00 (Deg); Cont. Scan Rate; 0.50 Deg/min.

The XRPD of crystalline form B of 5-Chloro-N2-(2-isopropoxy-5-methyl-4-piperidin-4-yl-phenyl)-N4-[2-(propane-2-sulfonyl)-phenyl]-pyrimidine-2,4-diamine exhibits diffraction peaks having maxima at diffraction angles 5.1°, 5.5°, 5.6°, 9.5°, 9.6°, 10.1°, 11.0°, 11.8°, 12.1°, 12.6°, 13.7°, 14.5°, 14.9°, 15.2°, 16.1°, 16.6°, 16.7°, 17.0°, 17.1°, 17.5°, 17.7°, 18.0°, 18.8°, 19.0°, 19.3°, 19.5°, 20.5°, 20.9°, 21.5°, 21.9°, 22.1°, 22.4°, 22.8°, 23.2°, 23.7°, 23.9°, 24.3°, 24.5°, 24.8°, 25.1°, 25.4°, 25.9°, 26.4°, 26.8°, 27.8°, 28.1°, 28.6°, 29.1°, 29.6°, 29.8°, 30.6°, 31.6°, 32.7°, 33.5°, 34.2°, 35.4°, 35.6° and 36.8° (2θ degrees), as summarized by the XRPD pattern in FIG. 4.

Figure 5:
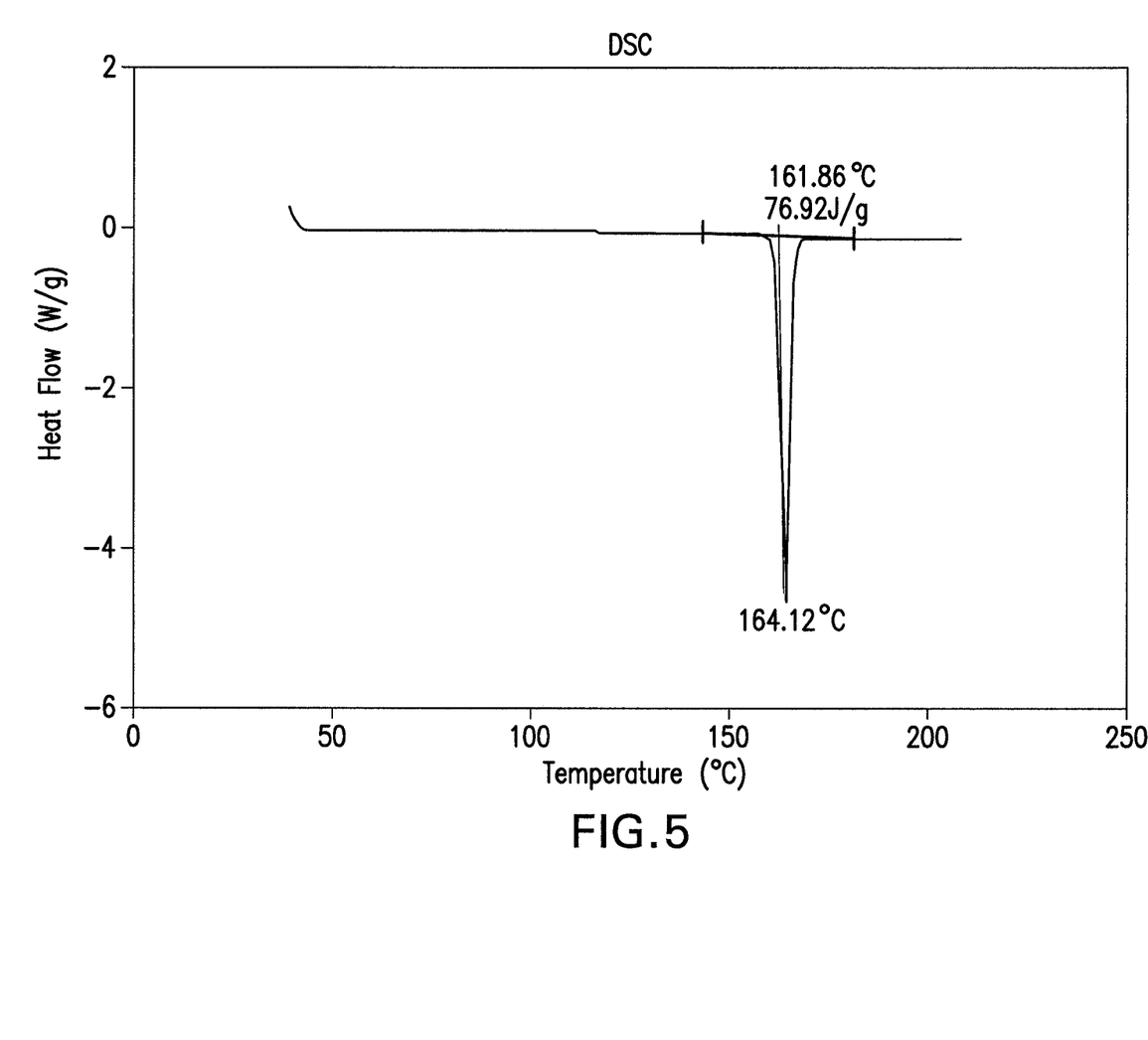
FIG. 5 depicts the differential scanning calorimetry curve for crystalline form B of 5-Chloro -N2-(2-isopropoxy-5-methyl-4-piperidin-4-yl-phenyl)-N4-[2-(propane-2-sulfonyl)-phenyl]-pyrimidine-2,4-diamine.
Figure 6:
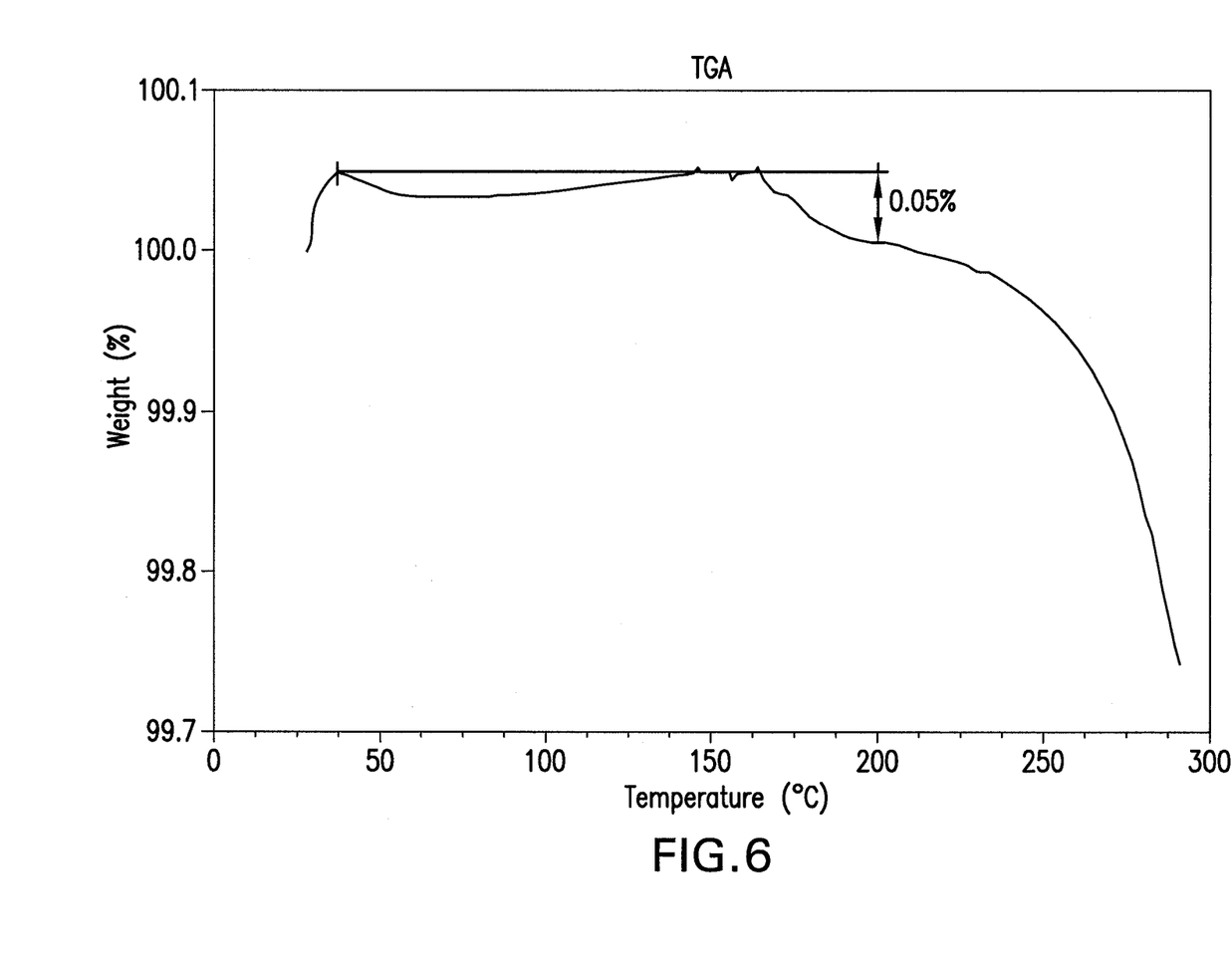
FIG. 6 depicts the thermogravimmetric plot for crystalline form B of 5-Chloro-N2-(2-isopropoxy-5-methyl-4-piperidin-4-yl-phenyl)-N4-[2-(propane-2-sulfonyl)-phenyl]-pyrimidine-2,4-diamine.

Crystalline form B of 5-Chloro-N2-(2-isopropoxy-5-methyl-4-piperidin-4-yl-phenyl) -N4-[2-(propane-2-sulfonyl)-phenyl]-pyrimidine-2,4-diamine exhibits the following thermal parameters: melting point, Tm (onset) 162° C. as determined by differential scanning calorimetry at a scanning rate of 10° C./min. (FIG. 5), decomposition point, T>250° C., and a weight loss on drying of 0.05% at 200° C., as determined by thermogravimmetric analysis and summarized in FIG. 6.

The Fourier Transform Infrared (FT-IR) spectrum of crystalline form B of 5-Chloro-N2-(2-isopropoxy-5-methyl-4-piperidin-4-yl-phenyl)-N4-[2-(propane-2-sulfonyl)-phenyl]-pyrimidine-2,4-diamine exhibits main bands (wavenumbers, cm$^{-1}$) at 3418.7, 3309.5, 3202.3, 2976.2, 2936.3, 2806.9, 2731.8, 1683.9, 1652.8, 1598.4, 1568.9, 1507.0, 1483.5, 1447.1, 1411.0, 1314.9, 1288.1, 1261.1, 1220.8, 1195.7, 1170.8, 1140.1, 1124.6, 1083.2, 1053.3, 1010.1, 947.1, 874.5, 776.0, 758.7, 734.5, 706.5, 678.5, 652.1, 586.3, 544.7, 519.1, 472.6, and 456.8.

In an exemplary embodiment, the present invention provides a method for the preparation substantially pure crystalline forms of 5-Chloro-N2-(2-isopropoxy-5-methyl-4-piperidin-4-yl-phenyl)-N4-[2-(propane-2-sulfonyl)-phenyl]-pyrimidine-2,4-diamine. The crystalline forms are prepared from a solvent or mixed solvents comprising a good solvent, in which the compound is readily soluble, and a poor solvent, in which it is more sparingly soluble, may also be employed provided that crystallization from the mixture is possible using the selected solvent mixture. Examples of good solvents include methanol, ethanol and isopropanol, formic acid, acetic acid, ethyl acetate, tetrahydrofuran and acetone. An example of a poor solvent is e.g., water.

In one embodiment, crystalline form A of 5-Chloro-N2-(2-isopropoxy-5-methyl-4-piperidin-4-yl-phenyl)-N4-[2-(propane-2-sulfonyl)-phenyl]-pyrimidine-2,4-diamine is prepared by reacting 5-Chloro-N2-(2-isopropoxy-5-methyl-4-piperidin-4-yl-phenyl)-N4-[2-(propane-2-sulfonyl)-phenyl]-pyrimidine-2,4-diamine dihydrochloride in aqueous acetone with at least two equivalents of aqueous sodium hydroxide. The ratio of acetone:water usefully employed in accordance with the invention ranges from 1:1 to 5:1 and 1:1 to 1:5 (volume:volume, v/v), including 1:1 and 3:1. The reaction temperature ranges from 20° to 70° C., including 55° C.

In one embodiment, the crystalline form A of 5-Chloro-N2-(2-isopropoxy-5-methyl-4-piperidin-4-yl-phenyl)-N4-[2-(propane-2-sulfonyl)-phenyl]-pyrimidine-2,4-diamine contains less than 1% by weight total impurities. In another embodiment, the polymorph form A contains less than 0.5% by weight total impurities. In yet another embodiment, the polymorph form A contains less than 0.1% by weight total impurities.

In another embodiment, crystalline form B of 5-Chloro-N2-(2-isopropoxy-5-methyl-4-piperidin-4-yl-phenyl)-N4-[2-(propane-2-sulfonyl)-phenyl]pyrimidine-2,4-diamine is prepared by reacting 5-Chloro-N2-(2-isopropoxy-5-methyl-4-piperidin-4-yl-phenyl)-N4-[2-(propane-2-sulfonyl)-phenyl]-pyrimidine-2,4-diamine with aqueous hydrochloric acid and subsequently adding sodium hydroxide. The reaction temperature ranges from 20° C. to 70° C.

In another embodiment, crystalline form B of 5-Chloro-N2-(2-isopropoxy-5-methyl-4-piperidin-4-yl-phenyl)-N4-[2-(propane-2-sulfonyl)-phenyl]-pyrimidine-2,4-diamine is converted to crystalline form A of 5-Chloro-N2-(2-isopropoxy-5-methyl-4-piperidin-4-yl-phenyl)-N4-[2-(propane-2-sulfonyl)-phenyl]-pyrimidine-2,4-diamine by adding a small amount of crystalline form A (1% by weight or less, referred to as seeding) to a suspension or solution of form B of 5-Chloro-N2-(2-isopropoxy-5-methyl-4-piperidin-4-yl-phenyl)-N4-[2-(propane-2-sulfonyl)-phenyl]-pyrimidine-2,4-diamine in aqueous acetone. The temperature usefully employed for seeding ranges from 20-40° C.

As used herein, the term "seed" can be used as a noun to describe one or more crystals of a crystalline compound of formula I. The term "seed" can also be used as a verb to describe the act of introducing said one or more crystals of a crystalline compound of formula I into an environment (including, but not limited to e.g., a solution, a mixture, a suspension, or a dispersion) thereby resulting in the formation of more crystals of the crystalline compound of formula I.

In another embodiment, crystalline form B of 5-Chloro-N2-(2-isopropoxy-5-methyl-4-piperidin-4-yl-phenyl)-N4-[2-(propane-2-sulfonyl)-phenyl]-pyrimidine-2,4-diamine is converted to crystalline form A of 5-Chloro-N2-(2-isopropoxy-5-methyl-4-piperidin-4-yl-phenyl)-N4-[2-(propane-2-sulfonyl)-phenyl]-pyrimidine-2, 4-diamine by heating a suspension or solution containing crystalline form B of 5-Chloro-N2-(2-isopropoxy-5-methyl-4-piperidin-4-yl-phenyl) -N4-[2-(propane-2-sulfonyl)-phenyl]-pyrimidine-2,4-diamine in aqueous acetone. Mixed solvents usefully employed include, for example, acetone/water and ethanol/water. In a preferred embodiment, the ratio of acetone:water usefully employed ranges from 1:1 to 5:1 (volume:volume, v/v), including 1:1 and 3:1. The reaction temperature ranges from 30° to 70° C., including 50° C.

In an exemplary embodiment, a pharmaceutical composition is provided comprising: (a) a therapeutically effective amount of a substantially pure crystalline form of 5-Chloro-N2-(2-isopropoxy-5-methyl-4-piperidin-4-yl-phenyl)-N4-[2-(propane-2-sulfonyl)-phenyl]-pyrimidine-2,4-diamine; and (b) at least one pharmaceutically acceptable carrier. In a preferred embodiment, the pharmaceutical composition comprises: (a) a therapeutically effective amount of a substantially pure crystalline form A of 5-Chloro-N2-(2-isopropoxy-5-methyl-4-piperidin-4-yl-phenyl)-N4[2-(propane-2-sulfonyl)-phenyl]-pyrimidine-2,4-diamine; and (b) at least one pharmaceutically acceptable carrier.

The at least one pharmaceutically acceptable carrier is in the form of a diluent, vehicle or excipient and can readily be selected by one of ordinary skill in the art and will be determined by the desired mode of administration. Illustrative examples of suitable modes of administration include oral, nasal, parenteral, topical, transdermal, and rectal. The pharmaceutical compositions of this invention may take any pharmaceutical form recognizable to the skilled artisan as being suitable. Suitable pharmaceutical forms include solid, semi-solid, liquid, or lyophilized formulations, such as tablets, powders, capsules, suppositories, suspensions, liposomes, and aerosols.

In an exemplary embodiment, use of a substantially pure crystalline form of 5-Chloro -N2-(2-isopropoxy-5-methyl-4-piperidin-4-yl-phenyl)-N4-[2-(propane-2-sulfonyl)-phenyl]-pyrimidine-2,4-diamine for the preparation of a medicament for the treatment of disorders mediated by anaplastic lymphoma kinase is provided. In a preferred embodiment, the medicament comprises: (a) a therapeutically effective amount of a substantially pure crystalline form A of 5-Chloro-N2-(2-isopropoxy-5-methyl-4-piperidin-4-yl-phenyl)-N4-[2-(propane-2-sulfonyl)-phenyl]-pyrimidine-2,4-diamine. The medicament is useful in treating diseases which respond to inhibition of anaplastic lymphoma kinase activity, focal adhesion kinase (FAK), zeta-chain-associated protein kinase 70 (ZAP-70) insulin-like growth factor (IGF-1R and combinations thereof. The diseases are selected from benign or malignant tumor; a cancer selected from anaplastic large cell lymphoma; non-Hodgkin's lymphoma; an inflammatory myofibrolastic tumor; a neuroblastoma; sarcoma; lung; bronchus; prostate; breast (including sporadic breast cancers and sufferers of Cowden disease); pancreas; gastrointestinal cancer; colon; rectum; colon carcinoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary; multiple myeloma; esophagus; a leukaemia; acute myelogenous leukemia; chronic myelogenous leukemia; lymphocytic leukemia; myeloid leukemia; brain; a carcinoma of the brain; oral cavity and pharynx; larynx; small intestine; and melanoma. A "therapeutically effective amount" is intended to mean the amount of the inventive crystalline form that, when administered to a subject in need thereof, is sufficient to effect treatment for disease conditions alleviated by the inhibition of protein kinase activity. The amount of a given compound of the invention that will be therapeutically effective will vary depending upon factors such as the disease condition and the severity thereof, the identity of the subject in need thereof, etc., which amount may be routinely determined by artisans of ordinary skill in the art. Preferably, more than 80%, more preferably at least 85%, still more preferably at least 90%, and most preferably at least 95%, of the crystalline form administered is of one of the inventive forms. As noted above, illustrative modes of administration include oral, nasal, parenteral, topical, transdermal, and rectal. Administration of the crystalline form may be accomplished by administration of a pharmaceutical composition of this invention or via any other effective means.

Specific embodiments of the invention will now be demonstrated by reference to the following examples. It should be understood that these examples are disclosed solely by way of illustrating the invention and should not be taken in any way to limit the scope of the present invention.

EXAMPLE 1

Preparation of Form A of 5-chloro-N-(2-isopropoxy-5-methyl-4-(piperidin-4-ylphenyl)-N-2-(isopropylsulfonyl)phenyl)-2,4-diamine 5-chloro-N-(2-isopropoxy-5-methyl-4-(piperidin-4-ylphenyl)-N-2-(isopropylsulfonyl)phenyl) -2,4-diamine di-hydrochloride salt The compound 2-isopropoxy-5-methyl-4-(piperdin-4-yl) aniline dihydrochloride (33.00 g, 85.25 mmol) and 2,5-dichloro-N-(2-(isopropyl sulfonyl)phenyl)pyrimidin-4-amine (32.53 g) was added to a 3-necked 500-mL round-bottomed flask equipped with mechanical stirring, thermocouple, reflux condenser and $N_2$ inlet-outlet. A solvent, 2-propanol (255.0 g, 325 mL), was added and the mixture to heated to reflux at 82±2° C. and stirred for at least 14 hours. The mixture was cooled to 22±3° C. over 1 hour and stirred at 22±3° C. for 3 hours. The resulting solids were filtered and rinsed with 3×40 g (3×51 mL) of 2-propanol. The solids were dried at 50±5° C./10 mbar for 16 hours to yield 44.63 g of 5-chloro-N-(2-isopropoxy-5-methyl-4-(piperidin-4-ylphenyl)-N-2-(isopropylsulfonyl)phenyl)-2,4-diamine di-hydrochloride salt. Chemical Purity (as determined by HPLC): 97.3%. Corrected yield: 71.6%. LOD=11.60%. The dihydrochloride salt was recrystallized using acetone:water (10:1, v/v). Chemical Purity (as determined by HPLC): 98.8%.

Form A of 5-chloro-N-(2-isopropoxy-5-methyl-4-(piperidin-4-ylphenyl)-N-2-(isopropylsulfonyl)phenyl)-2,4-diamine 7.00 g of 5-chloro-N-(2-isopropoxy-5-methyl-4-(piperidin-4-yl) phenyl)-N-(2-(isopropylsulfonyl)phenyl)-2,4-diamine di-hydrochloride and 21.0 g of acetone:water (3:1, v/v) was added to a dry and clean crystallizer at ambient temperature. The mixture was heated to 55±3° C. in about 20 minutes to obtain a clear solution. The hot solution was filtered and 2.6 g of acetone and water was added to the mixture. While heating was maintained, 14.69 g (about 58% by weight) of aqueous NaOH solution was added over a period of about 0.5 hour. The reaction mixture was maintained at 55±3° C. for an additional 2 hours to yield an off-white slurry. An additional 10.82 g (about 58% by weight) of aqueous NaOH solution was added to the hot solution over a period of 1.5 hours to yield a thick off-white slurry. The slurry was cooled to 20±3° C. over a period of about 45 minutes and 47.0 g of deionized (DI) water was added over about 30 minutes and the off-white slurry was stirred at 20±3° C. for 1 hour. The slurry was filtered and rinsed with 2×25.0 g of DI water. The wet cake was dried about 17 hours in a vacuum oven at 50±3° C. and 10 mbar under a $N_2$ purge to yield 6.06 g off-white or tan solid, 5.30 g of 5-chloro-N-(2-isopropoxy-5-methyl-4-(piperidin-4-yl) phenyl)-N-(2-(isopropylsulfonyl)phenyl)-2,4-diamine. Yield: 87.5%. Form A was identified and confirmed by its corresponding XRPD pattern, FT-IR and thermal parameters.

EXAMPLE 2

Preparation of Form B of 5-chloro-N-(2-isopropoxy-5-methyl-4-(piperidin-4-ylphenyl)-N-2-(isopropylsulfonyl)phenyl)-2,4-diamine 5.58 g of 5-chloro-N-(2-isopropoxy-5-methyl-4-(piperidin-4-yl) phenyl)-N-(2-(isopropylsulfonyl)phenyl)-2,4-diamine was dissolved in 50 mL of 1.0 N HCl at 30-40° C. to afford a clear solution. 200 mL of 0.3 N NaOH was added this clear solution dropwise over 20 minutes at 20-23° C. A cloudy mixture was obtained, which was heated with stirring at 40-42° C. for 2 hours and subsequently heated to 50-55° C. for 2 hours. The resulting slurry was cooled to room temperature and the slurry was filtered. The wet cake was washed with 3×20 mL of water and dry under vacuum to obtain 5.30 g off white solid. Yield: 95%. Form B was identified and confirmed by s corresponding XRPD pattern, FT-IR and thermal parameters.

EXAMPLE 3

Preparation of Form A of 5-chloro-N-(2-isopropoxy-5-methyl-4-(piperidin-4-ylphenyl)-N-2-(isopropylsulfonyl)phenyl)-2,4-diamine by seeding a suspension of Form B of 5-chloro-N-(2-isopropoxy-5-methyl-4-(piperidin-4-ylphenyl)-N-2-(isopropylsulfonyl)phenyl)-2,4-diamine with Form A A small amount of crystalline form A of 5-chloro-N-(2-isopropoxy-5-methyl-4-(piperidin-4-ylphenyl)-N-2-(isopropylsulfonyl)phenyl)-2,4-diamine (0.1-1.0% by weight) was added to a suspension of crystalline form B of 5-chloro-N-(2-isopropoxy-5-methyl-4-(piperidin -4-ylphenyl)-N-2-(isopropylsulfonyl)phenyl)-2,4-diamine in aqueous acetone with stirring at room temperature. The crystalline form was analyzed by its corresponding turbidity profile or by XRPD. The amount of substantially pure form A obtained is influenced by the solvent, ratio of acetone to water by volume and the amount of "seed" A used, as summarized in Table 1.

TABLE 1

Seeding of Crystalline Form B with Form A.

| Solvent System Acetone:water (v/v) | Form A "Seed" (weight %) | XRPD after 24 hours |
|---|---|---|
| 1:9 | 1.0 | Form B + Form A |
| 1:9 | 0.1 | Form B |
| 3:7 | 1.0 | Form A |
| 3:7 | 0.1 | Form B + Form A |
| 1:1 | 1.0 | Form A (at 2 hours) |
| 1:1 | 0.1 | Form A (at 4 hours) |

EXAMPLE 4

Conversion of Form B of 5-chloro-N-(2-isopropoxy-5-methyl-4-(piperidin-4-ylphenyl)-N-2-(isopropylsulfonyl)phenyl)-2,4-diamine to Form A of 5-chloro-N-(2-isopropoxy-5-methyl-4-(piperidin-4-ylphenyl)-N-2-(isopropylsulfonyl)phenyl)-2,4-diamine by heating in an aqueous solvent A suspension of crystalline from B of 5-chloro-N-(2-isopropoxy-5-methyl-4-(piperidin-4-ylphenyl)-N-2-(isopropylsulfonyl)phenyl)-2,4-diamine was heated in an aqueous solvent with stirring. The conversion of crystalline form B to crystalline form A was analyzed by its corresponding turbidity profile or by XRPD. The amount of substantially pure form A obtained and its corresponding time of conversion is influenced by the solvent system and temperature, as summarized in Table 2.

TABLE 2

Conversion of Crystalline Form B to Crystalline Form A.

| Solvent System (v/v) | Temp. (° C.) | Conv. Time (hours) | Induction Time (hours) | Yield (%) |
|---|---|---|---|---|
| 1:1 acetone:water | 35 | >3 | — | — |
| 1:1 acetone:water | 40 | 2 | 1 | 99.1 |
| 1:1 acetone:water | 50 | 1.5 | 0.1 | 97.6 |
| 1:1 ethanol:water | 35 | 2 | 38 | >99 |
| 1:1 ethanol:water | 50 | 1 | 4 | >99 |

The invention claimed is:

1. A crystalline form of 5-Chloro-N2-(2-isopropoxy-5-methyl-4-piperidin-4-yl-phenyl)-N4-[2-(propane-2-sulfonyl)-phenyl]pyrimidine-2,4-diamine exhibiting one or more X-ray powder diffraction peaks having maxima at diffraction angles selected from 7.2°, 8.1°, 10.8°, 12.0°, 12.4°, 13.4°, 14.4°, 14.8°, 15.7°, 16.9°, 17.7°, 18.5°, 19.0°, 19.5°, 20.0°, 20.3°, 21.1°, 21.6°, 22.4°, 22.6°, 23.0°, 24.1°, 24.5°, 25.5°, 26.0°, 26.2°, 27.0°, 27.3°, 28.3°, 29.0°, 29.1°, 30.6°, 31.3°, 32.8°, 33.5°, 34.2° and 36.4° (2θ degrees).

2. The crystalline form of claim 1, having a melting point of 174° C., as determined by differential scanning calorimetry.

3. The crystalline form of claim 1, having a decomposition point greater than 250° C. and a weight loss on drying of 0.1% at 200° C., as determined by thermogravimmetric analysis.

4. The crystalline form of claim 1, having characteristic infrared absorption bands at 3440.4, 3318.9, 2973.7, 2931.3, 2921.7, 1596.8, 1562.1, 1498.4, 1442.5, 1409.7, 1382.7, 1311.4, 1284.4, 1270.9, 1251.6, 1224.6, 1139.7, 1126.2, 1139.7, 1126.2, 1105.0, 1081.9, 1049.1, 1020.2, 1012.5, 952.7, 937.3, 894.8, 877.5, 860.1, 848.5, 817.7, 798.4, 781.0, 763.7, 756.0, 732.8, 686.6, 665.3, 644.1, 586.3 and 543.8 (in units of wavenumbers, cm $^{-1}$).

5. The crystalline form of claim 1, having less than 1.0% by weight total impurities.

6. The crystalline form of claim 1, having less than 0.5% by weight total impurities.

7. The crystalline form of claim 1, having less than 0.1% by weight total impurities.

8. A crystalline form of 5-Chloro-N2-(2-isopropoxy-5-methyl-4-piperidin-4-yl-phenyl)-N4-[2-(propane-2-sulfonyl)-phenyl]-pyrimidine-2,4-diamine exhibiting one or more X-ray powder diffraction peaks having maxima at diffraction angles selected from 5.1°, 5.5°, 5.6°, 9.5°, 9.6°, 10.1°, 11.0°, 11.8°, 12.1°, 12.6°, 13.7°, 14.5°, 14.9°, 15.2°, 16.1°, 16.6°, 16.7°, 17.0°, 17.1°, 17.5°, 17.7°, 18.0°, 18.8°, 19.0°, 19.3°, 19.5°, 20.5°, 20.9°, 21.5°, 21.9°, 22.1°, 22.4°, 22.8°, 23.2°, 23.7°, 23.9°, 24.3°, 24.5°, 24.8°, 25.1°, 25.4°, 25.9°, 26.4°, 26.8°, 27.8°, 28.1°, 28.6°, 29.1°, 29.6°, 29.8°, 30.6°, 31.6°, 32.7°, 33.5°, 34.2°, 35.4°, 35.6° and 36.8° (2θ degrees).

9. The crystalline form of claim 8, having a melting point of 162° C., as determined by differential scanning calorimetry.

10. The crystalline form of claim 8, having a decomposition point greater than 250° C. and a weight loss on drying of 0.05% at 200° C., as determined by thermogravimmetric analysis.

11. The crystalline form of claim 8, having characteristic infrared absorption bands at 3418.7, 3309.5, 3202.3, 2976.2, 2936.3, 2806.9, 2731.8, 1683.9, 1652.8, 1598.4, 1568.9, 1507.0, 1483.5, 1447.1, 1411.0, 1314.9, 1288.1, 1261.1, 1220.8, 1195.7, 1170.8, 1140.1, 1124.6, 1083.2, 1053.3, 1010.1, 947.1, 874.5, 776.0, 758.7, 734.5, 706.5, 678.5, 652.1, 586.3, 544.7, 519.1, 472.6, and 456.8 (in units of wavenumbers, cm $^{-1}$).

12. The crystalline form of claim 8, having less than 1.0% by weight total impurities.

13. The crystalline form of claim 8, having less than 0.5% by weight total impurities.

14. The crystalline form of claim 8, having less than 0.1% by weight total impurities.

15. A pharmaceutical composition comprising a crystalline from of claim 1, and a pharmaceutically acceptable carrier.

16. A pharmaceutical composition comprising a crystalline from of claim 8, and a pharmaceutically acceptable carrier.

17. A method for the preparation of a crystalline form of 5-Chloro-N2-(2-isopropoxy -5-methyl-4-piperidin-4-yl-phenyl)-N4-[2-(propane-2-sulfonyl)-phenyl]-pyrimidine-2,4-diamine which comprises the step of: reacting 5-Chloro-N2-(2-isopropoxy-5-methyl-4-piperidin-4 -yl-phenyl)-N4-[2-(propane-2-sulfonyl)-phenyl]-pyrimidine-2,4-diamine dihydrochloride in a solvent with at least two equivalents of aqueous sodium hydroxide.

18. The method of claim 17, wherein the solvent is acetone:water (3:1) by volume.

19. The method of claim 18, further comprising heating the reactants at a temperature ranging from 30-70° C.

20. The method of claim 18, further comprising heating the reactants at a temperature of 55° C.

21. A method for converting crystalline form B of 5-Chloro-N2-(2-isopropoxy-5-methyl-4-piperidin-4-yl-phenyl)-N4-[2-(propane-2-sulfonyl)-phenyl]-pyrimidine-2,4-diamine to crystalline form A of 5-Chloro-N2-(2-isopropoxy-5-methyl-4-piperidin-4-yl-phenyl)-N4-[2-(propane-2-sulfonyl)-phenyl]-pyrimidine-2,4-diamine by adding a small amount of crystalline form A to a suspension of form B of 5-Chloro-N2-(2-isopropoxy-5-methyl-4-piperidin-4-yl-phenyl)-N4-[2-(propane-2-sulfonyl)-phenyl]-pyrimidine-2,4-diamine in a solvent.

22. The method of claim 21, wherein the amount of form A added is 1.0% by weight or less.

23. The method of claim 22, the solvent is acetone:water (1:1) by volume at a temperature ranging from 20-40° C.

24. A method for converting crystalline form B of 5-Chloro-N2-(2-isopropoxy-5-methyl-4-piperidin-4-yl-phenyl)-N4-[2-(propane-2-sulfonyl)-phenyl]-pyrimidine-2,4-diamine to crystalline form A of 5-Chloro-N2-(2-isopropoxy-5-methyl-4piperidin-4-yl-phenyl)-N4-[2-(propane-2-sulfonyl)-phenyl]-pyrimidine-2,4-diamine by heating a suspension of form B of 5-Chloro-N2-(2-isopropoxy-5-methyl-4-piperidin-4-yl-phenyl)-N4-[2-(propane-2-sulfonyl)-phenyl]-pyrimidine-2,4-diamine in a solvent.

25. The method of claim 24, the solvent is acetone:water 1:1 to 5:1 by volume at temperature ranging from 30° to 70° C.

26. The method of claim 24, the solvent is acetone:water 1:1 by volume at temperature of 50° C.

\* \* \* \* \*